(12) United States Patent
Plutzky et al.

(10) Patent No.: US 9,078,852 B2
(45) Date of Patent: Jul. 14, 2015

(54) RETINALDEHYDE IN THE TREATMENT OF OBESITY, DIABETES AND OTHER CONDITIONS

(75) Inventors: Jorge Plutzky, Chestnut Hill, MA (US); Ouliana Ziouzenkova, Columbus, OH (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 890 days.

(21) Appl. No.: 12/919,716

(22) PCT Filed: Feb. 27, 2009

(86) PCT No.: PCT/US2009/001238
§ 371 (c)(1),
(2), (4) Date: Nov. 1, 2010

(87) PCT Pub. No.: WO2009/110983
PCT Pub. Date: Sep. 11, 2009

(65) Prior Publication Data
US 2011/0046234 A1 Feb. 24, 2011

Related U.S. Application Data

(60) Provisional application No. 61/064,375, filed on Feb. 29, 2008.

(51) Int. Cl.
*A61K 31/11* (2006.01)
*A61P 3/10* (2006.01)
*A61P 3/04* (2006.01)
*A61P 35/00* (2006.01)
*A61P 9/10* (2006.01)

(52) U.S. Cl.
CPC ..................................... *A61K 31/11* (2013.01)

(58) Field of Classification Search
CPC ...................................................... A61K 31/11
USPC .......................................................... 514/703
See application file for complete search history.

(56) References Cited

U.S. PATENT DOCUMENTS

| | | |
|---|---|---|
| 5,489,611 A | 2/1996 | Lee et al. |
| 6,869,603 B2 | 3/2005 | Plutzky et al. |
| 7,030,265 B2 | 4/2006 | Sin et al. |
| 2003/0119715 A1 | 6/2003 | Ward et al. |
| 2005/0175555 A1 | 8/2005 | Stradi et al. |

FOREIGN PATENT DOCUMENTS

WO    WO 2004066912 A2 *  8/2004

OTHER PUBLICATIONS

Minsheng Yuan, Nicky Konstantopoulos, Jongsoon Lee, Lone Hansen, Zhi-Wei Li, Michael Karin, Steven E. Shoelson; Reversal of Obesity-and Diet-Induced Insulin Resistance with Salicylates or Targeted Disruption of Ikkb Science vol. 293 Aug. 31, 2001, 1673-1677.*
Zainab M. Al-Amin, Martha Thomson, Khaled K. Al-Qattan, Riitta Peltonen-Shalaby and Muslim Ali, Anti-diabetic and hypolipidaemic properties of ginger (Zingiber officinale) in streptozotocin-induced diabetic rats, British Journal of Nutrition (2006), 96, 660-666.*
International Search Report for PCT/US2009/001238 filed Feb. 27, 2009.
Written Opinion of the International Searching Authority for PCT/US2009/001238 filed Feb. 27, 2009.
International Preliminary Report on Patentability for PCT/US2009/001238 filed Feb. 27, 2009.
Asatryan, et al., "Heme and lipid peroxides in hemoglobin-modified low-density lipoprotein mediate cell survival and adaptation to oxidativie stress," *Blood* 102(5):1732-1739 (Sep. 2003).
Ahmed, et al., "High-Density Lipoprotein Hydrolysis by Endothelial Lipase Activates PPARα," *Circ. Res.* 98:490-498 (2006).
Canan Koch, et al., "Synthesis of Retinoid Receptor-Specific Ligands That Are Potent Inducers of Adipogenesis in 3T3-L1 Cells," *J. Med. Chem.* 42:742-750 (1999).
Cavasotto, et al., "Determinants of Retinoid X Receptor Transcriptional Antagonism," *J. Med. Chem.* 47:4360-4372 (2004).
Chambon, et al., "A decade of molecular biology of retinoic acid receptors," *FASEB J.* 10:940-954 (1996).
Duester, et al., "Cytosolic retinoid dehydrogenases govern ubiquitous metobolism of retinol to retinaldehyde followed by tissue-specific metabolism to retinoic acid," *Chem. Biol. Interact.* 143-144:201-210 (2003).
Duester, et al., "Families of retinoid dehydrogenases regulating vitamin A function," *Eur. J. Biochem.* 267:4315-4324 (2000).
Fu, et al., "A Nuclear Receptor Atlas: 3T3-L1 Adipogenesis," *Mol. Endocrinol.* 19:2437-2450 (2005).
Graham, et al., "Retinol-Binding Protein 4 and Insulin Resistance in Lean, Obese, and Diabetic Subjects," *N. Engl. J. Med.* 354:2552-2563 (Jun. 2006).
Heyman, et al., "9-Cis Retinoic Acid Is a High Affinity Ligand for the Retinoid Receptor," *Cell* 68:397-406 (Jan. 1992).
Imai, et al., "Impaired adipogenesis and lipolysis in the mouse upon selective ablation of the retinoid X receptor α mediated by a tamoxifen-inducible chimeric Cre recombinase (Cre-ER$^{72}$) in adipocytes," *PNAS* 98(1):224-228 (Jan. 2001).
Kalajdzic, et al., "Nimesulide, a Preferencial Cyclooxygenase 2 Inhibitor, Suppresses Peroxisome Proliferator-Activated Receptor Induction of Cyclooxygenase 2 Gene Expression in Human Synovial Fibroblasts," *Arthritis Rheum.* 46(2):494-506 (Feb. 2002).
Kanayasu-Toyoda, et al., "HX531, a retinoid X receptor antagonist, inhibited the 9-cis retinoic acid-induced binding with steroid receptor coactivator-1 as detected by surface plasmon resonance," *Steroid Biochem. Mol. Biol.* 94:303-309 (2005).

(Continued)

*Primary Examiner* — Kendra D Carter
*Assistant Examiner* — Jason A Deck
(74) *Attorney, Agent, or Firm* — Law Office of: Michael A. Sanzo, LLC

(57) ABSTRACT

The present invention is directed to methods of treating a patient for a disease or condition associated with adipogenesis or insulin resistance by administering a retinaldehyde compound to the patient or a compound that increases endogenous retinaldehyde levels by inhibiting the enzyme retinaldehyde dehydrogenase 1.

18 Claims, No Drawings

(56) References Cited

OTHER PUBLICATIONS

Kanda, et al., "PPARγ in the endothelium regulates metabolic responses to high-fat diet in mice," *J. Clin. Invest.* 119(1):110-124 (Jan. 2009).
Knowles, et al., "The Preparation of 11-*Cis*-Retinal," *Vison Res.* 18:115-116 (1978).
Michalik, et al., "International Union of Pharmacology. LXI. Peroxisome Proliferation-Activated Receptors," *Pharmacol. Rev.* 58(4):726-741 (2006).
Molotkov, et al., "Genetic Evidence That Retinaldehyde Dehydrogenase *Raldh 1* (*Aldh 1 a 1*) Functions Downstream of Alcohol Dehydrogenase *Adh1* in Metabolism of Retinol to Retinoic Acid," *J. Biol. Chem.* 278(38):36085-36090 (2003).
Napoli, "Retinoic Acid: Its Biosynthesis and Metabolism," *Prog. Nucleic Acid Res. Mol. Biol.* 63:139-188 (1999).
Ohta, et al., "Novel retinoid X receptor (RXR) antagonists having a dicarba-*closo*-dodecaborane as a hydrophobic moiety," *Bioorg. Med. Chem. Lett.* 14:5913-5918 (2004).
Ress, et al., "Toxicology and Carcinogenesis Studies of Microencapsulated Citral in Rats and Mice," *Toxicol. Sci.* 71:198-206 (2003).
Rieusset, et al., "A New Selective Peroxisome Proliferator-Activated Receptor γ Antagonist with Antiobesity and Antidiabetic Activity," *Mol. Endocrinol.* 16(11):2628-2644 (Nov. 2002) and erratum *Mol. Endocrinol.* 16(12):2745 (Dec. 2002).
Shulman, et al., "Retinoid X Receptor Heterodimers in te Metabolic Syndrome," *N. Eng. J. Med.* 353(6):604-615 (Aug. 2005).
Takahashi, et al., "Novel Retinoid X Receptor Antagonists: Specific Inhibition of Retinoid Synergism in RXR-RAR Heterodimer Actions," *J. Med. Chem.* 45(16):3327-3330 (Aug. 2002).
Takitani, et al., "Retinal is a modulator repressing adipogenesis,"*Bitamin* 81(11):575-577 (2007) with English language translation attached.
Wada, et al., "A Highly Stereoselective Synthesis of 11Z-Retinal Using Tricarbonyliron Complex," *J. Org. Chem.* 65:2438-2443 (2000).
Xeu, et al., "Distinct Stages in Adipogenesis Revealed by Retinoid Inhibition of Differentiation after Induction of PPARγ," *Mol. Cell. Biol.* 16(4):1567-1575 (Apr. 1996).
Yamauchi, et al., "Inhibition of RXR and PPARγ ameliorates diet-induced obesity and type 2 diabetes," *J. Clin. Invest.* 108(7):1001-1013 (Oct. 2001).
Yang, et al., "Serum retinol binding protein 4 contributes to insulin resistance in obesity and type 2 diabetes," *Nature* 436:356-362 (Jul. 2005).
Ziouzenkova, et al., "Abstract 1556: Retinaldehyde Inhibits Adipogenesis Through RXR and PPAR-gamma Repression," *Circulation* 114:301 (2006).
Ziouzenkova, et al., "Retinoid metabolism and nuclear receptor responses: New insights into coordinated regulation of the PPAR-RXR complex," *Febs Lett.* 582(1):32-38 (2008).
Ziouzenkova, et al., "Dual Roles for Lipolysis and Oxidation in Peroxisome Proliferation- Activator Receptor Responses to Electronegative Low Density Lipoprotein," *J. Biol. Chem.* 278(41):39874-39881 (Oct. 2003).
Ziouzenkova, et al., "Asymmetric Cleavage of β-Carotene Yields a Transcriptional Repressor of Retinoid X Receptor and Peroxisome Proliferator-Activated Receptor Response," *Mol. Endocrinol.* 21(1):77-88 (2007).
Ziouzenkova, et al.,"Retinaldehyde represses adipogenesis and diet-induced obesity," *Nature Medicine* 13(6):695-702 (Jun. 2007).
Ziouzenkova, et al.,"Lipolysis of triglyceride-rich lipoproteins generates PPAR ligands: Evidence of an antiinflammatory role for lipoprotein lipase," *PNAS* 100(5):2730-2735 (Mar. 2003).
Tesch, et al., "Rodent models of streptozotocin-induced diabetic nephropathy" *Nephrology* 12:261-266 (2007).

\* cited by examiner

RETINALDEHYDE IN THE TREATMENT OF OBESITY, DIABETES AND OTHER CONDITIONS

CROSS REFERENCE TO RELATED APPLICATIONS

Cross Reference to Related Applications

The present application is US national stage of international application PCT/US2009/001238, which had an international filing date of Feb. 27, 2009, and which claims the benefit of U.S. provisional application 61/064,375 filed on Feb. 29, 2008. The contents of this prior application is hereby incorporated by reference in its entirety. The international application was published in English under PCT Article 21(2) on Sep. 11, 2009.

FIELD OF THE INVENTION

The present invention is directed to methods of treating patients for obesity or diabetes by increasing effective cellular levels of retinaldehyde (Rald). This may be accomplished by administering retinaldehyde itself, a retinaldehyde derivative or a compound that inhibits retinaldehyde dehydrogenase1, an enzyme that is needed for cells to metabolize Rald. The inhibition of fat formation by Rald and Raldh1 inhibitors also establish a role for these molecules in treating liposarcomas, lipomas and other fat-based tumors and cancers as well as in the prevention or treatment of atherosclerosis.

BACKGROUND OF THE INVENTION

The retinoids are a group of compounds that are structurally related to vitamin A and that are used in the treatment of many diseases, especially diseases of the skin. Retinoic acid (RA), the most studied metabolite in the vitamin A pathway, exerts a broad range of biologic effects by controlling gene expression. RA binds to and activates the nuclear retinoic acid receptors (RAR) and retinoid X receptors (RXR)—transcription factors that link vitamin A metabolism to the transcriptional regulation of specific gene cassettes (Chambon, *Faseb J* 10, 940-54 (1996); Heyman, et al., *Cell* 68:397-406 (1992); Shulman, et al., *N. Engl. J. Med.* 353:604-15 (2005)). Retinoid X receptors also control key metabolic pathways by serving as the obligate heterodimeric partner for multiple steroid hormone nuclear receptor family members, including peroxisome proliferator-activated receptors (PPARs; Shulman, et al., *N. Engl. J. Med.* 353:604-15 (2005)). PPAR's are known to exist in three different isotypes, PPAR-alpha, PPAR-delta and PPAR-gamma.

RA also plays a role in adipogenesis, a differentiation process regulated by the complex interaction of multiple RXR heterodimeric partners (Fu, et al., *Mol. Endocrinol.* 19:2437-50 (2005)). RA effects appear to vary as a function of the stage of adipogenesis and relative RAR, PPARγ, and RXR expression (Fu, et al., *Mol. Endocrinol.* 19:2437-50 (2005); Xue, et al., *Mol. Cell. Biol.* 16:1567-75 (1996)). Early in adipogenesis, RA blocks differentiation, whereas, after 48 hours of differentiation, RA promotes fat cell formation (Xue, et al., *Mol. Cell. Biol.* 16:1567-75 (1996)). Divergent effects of RA on adipogenesis likely derives from differential actions of specific configurations of RA (all trans vs 9 cis RA) and the interaction of these different molecules with distinct nuclear receptors, namely RAR and RXR). This data highlights the importance of specific retinoid molecules and metabolites.

In contrast to the broad range of biological effects associated with RA, a role for Rald outside the eye remains essentially unknown (Napoli, *Prog. Nucleic Acid Res. Mol. Biol.* 63:139-88 (1999)). Rald is considered primarily a precursor for RA formation (Duester, et al., *Chem. Biol. Interact.* 143-144:201-10 (2003); Duester, *Eur. J. Biochem.* 267:4315-24 (2000)). Alcohol dehydrogenases (Adh) oxidize retinol (vitamin A) to Rald while retinaldehyde dehydrogenases (Raldh) help reduce cellular levels by oxidizing Rald to RA (Duester, et al., *Chem. Biol. Interact.* 143-144:201-10 (2003)). A toxicology study on citral, an inhibitor of Raldh, demonstrated that citral at high doses was well tolerated in rats and that rats fed a diet with citral weighed less than animals fed a citral free diet (Ress, et al., *Toxicol. Sci.* 71:198-206 (2003)).

SUMMARY OF THE INVENTION

General Summary

The present invention is based upon experimental results demonstrating that Rald is present in fat in vivo where it functions as a previously unrecognized regulator of adipogenesis, exerting effects specific to Rald and independent of its conversion to RA. Rald's effects appear to be mediated by its binding to RXR and PPARγ receptors, inhibiting the action of the required transcriptional complex that exists between RXR and PPARs. All three major Rald isomers, namely 9-cis, 13-cis, and all-trans Rald were found to be effective receptor binders (Kd=5.9±0.7, 9.7±1.2, and 11.9±1.9 for 9-cis, 13-cis, and all-trans Rald, respectively). When administered to rats, Rald was found to suppress both adipogenic gene expression and adipocyte lipid accumulation and, unlike RA, its effects did not appear to vary with the developmental stage of animals. These results suggest that Rald should be effective in treating or preventing obesity. In addition, Raldh1$^{-/-}$ mice showed reduced insulin resistance/diabetes in response to a high fat diet, suggesting that Rald should also be useful in the treatment or prevention of diabetes. Similar responses are also observed in the ob/ob model of obesity.

Another aspect of this invention is the discovery that Rald, Rald-derived molecules or Raldh1 inhibitors should be useful in treating liposarcomas, lipomas or other fat-based tumors or cancers. Liposarcomas are commonly lethal as a result of their space occupying nature, for example in the chest (mediastinum) or head (cranium). Attempts to differentiate these fat cells into less dangerous cells, for example using PPAR-g agonists, have not been successful. Results obtained indicate that the injection of Rald, Rald-derived molecules or Raldh1 inhibitors will block fat tumors from expanding and may also induce shrinkage of such tumors. Lipomas are benign deposits of fat cells that often require surgical excision. Rald, Rald-derived molecules or Raldh1 inhibitors will allow treatment of these fatty tumors through simple injection.

SPECIFIC EMBODIMENTS

In its first aspect, the invention is directed to a method of treating a patient for a disease or condition associated with adipogenesis or insulin resistance by administering a therapeutically effective amount of retinaldehyde or a retinaldehyde derivative that maintains the ability to effectively bind to RXR-PPARγ complex. For the purposes of the present invention, the phrase "a disease or condition associated with adipogenesis or insulin resistance" includes obesity, diabetes, atherosclerosis, and a tumor or cancer of adipose tissue, e.g., a liposarcoma or lipoma. The term "retinaldehyde derivative" refers to a compound having the core structure of formula I:

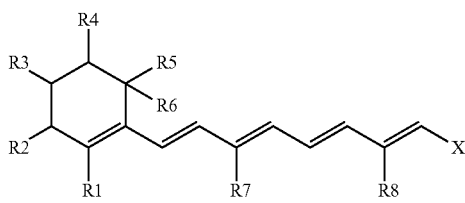

(I)

and which maintains the ability to effectively bind to RXR-PPARγ and repress its activity in a manner like retinaldehyde, as determined using standard assays such as those used in the experiments described in the Examples section herein. Effective binding means binding with a Kd of less than 100 μM preferably less than 50 μM and more preferably less than 20 μM. Unless otherwise indicated, all isomeric forms of compounds meeting these criteria are encompassed by the invention and compounds may be used in any pharmaceutically acceptable form. For example, any pharmaceutically acceptable salt form may be administered.

A "therapeutically effective amount" will be an amount sufficient to achieve the therapeutic objective for which a compound is administered. For example, it may be the amount necessary to prevent weight gain or promote weight loss in an overweight individual or the amount needed to reduce insulin resistance in a diabetic patient. In the case of tumors of adipose tissue, an therapeutically effective dose would be an amount sufficient to reduce tumor size or slow cancer progression. Similarly, in the case of atherosclerosis, a sufficient amount of compound should be given to reduce the growth or development of atherosclerotic plaques. In all cases, the daily dosage of active compound should typically be in the range of 50 μg-10 mg, preferably 100 μg-5 mg, and more preferably 500 μg-3 mg.

In general, an obese person is considered to be someone with a body mass index (BMI) of greater than 30 or with greater than 25% body fat. However, for the purposes of the present invention, the term will also be used to include people that are overweight to a lesser degree, with a BMI of greater than 25 or greater than 20% body fat. Compounds may also be used in people with a normal body weight to help prevent weight gain.

With respect to diabetes, the compounds will be of primary use in treating insulin resistance associated with type 2 diabetes. However, since patients with type 1 diabetes also sometimes develop insulin resistance, the compounds may be useful with these patients as well.

Preferred compounds are those having the basic structure shown in formula I in which: R1-R8 is each independently selected from: H, Cl; F; NO$_2$; I; Br; and a straight or branched C$_1$-C$_3$ alkyl; and X is C(=O)H; CN; or C(=O)R, where R is a C$_1$-C$_3$ alkyl. Especially preferred compounds are those in which at least one, and preferably all, of R1, R7 and R8 are methyl groups; X is C(=O)H; either, and preferably both, of R5 and R6 are methyl groups; and at least one, and preferably all of R2, R3 and R4 are hydrogens.

In another aspect, the invention is directed to a method of treating a patient for a disease or condition associated with adipogenesis or insulin resistance by administering a therapeutically effective amount of a compound that inhibits retinaldehyde dehydrogenase1 (Raldh1) activity. Included among inhibitors that may be used are the derivatives of citral described in U.S. Pat. No. 7,309,795, incorporated herein by reference in its entirety. These compounds may be in any isomeric form and be administered in any pharmaceutically acceptable form provided that they continue to promote weight loss or reduce insulin resistance as described in the Examples section herein. Daily dosages are expected to be in the range of 10 mg-100 g, preferably 50 mg-50 g, more preferably 100 mg-15 g, and still more preferably 500 mg-10 g. Preferred compounds are citral and derivatives of citral of formula II:

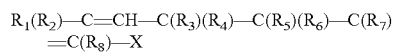

(III)

in which R$_1$-R$_8$ is each independently selected from: H, Cl; F; NO$_2$; I; Br; a straight or branched C$_1$-C$_6$ alkyl optionally substituted at one or more carbons with a substituent selected from: Cl; F; NO$_2$; I; Br; a C$_1$-C$_3$ alkyl; a straight or branched C$_2$-C$_6$ alkenyl optionally substituted at one or more carbons with a substituent selected from: Cl; F; NO$_2$; I; Br; a C$_1$-C$_3$ alkyl; and X is C(=O)H; CN; or C(=O)R wherein R is a C$_1$-C$_3$ alkyl.

Especially preferred compounds are those having the basic structure shown in formula II in which: either R$_1$ or R$_2$, and preferably both, are methyl groups; X is C(=O)H; one of R$_3$ or R$_4$ is a methyl and the other is H; one of R$_5$ or R$_6$ is a methyl and the other is H; R$_7$ is a methyl group; and R$_8$ is hydrogen.

DETAILED DESCRIPTION OF THE INVENTION

A. Compounds

Retinaldehyde is sold commercially as an ingredient in topical compositions for treating skin conditions and as a research reagent by Sigma-Aldrich Inc. (St. Louis, Mo.). Methods for chemically synthesizing and purifying retinal have long been known in the art (see e.g., Knowles, et al., *Vision Res.* 18:115-116 (1978); Wanda, et al., *J. Org. Chem.* 65(8):2438-43 (2000)) and all of the derivatives described herein can be made using methods applied to closely related compounds as a guide (see e.g., U.S. Pat. No. 7,030,265).

Citral, 3,7-dimethyl-2,6-octadienal, has a lemon scent and taste and is commonly used commercially as a flavoring agent and as a perfume. It is available in large amounts from many commercial suppliers and methods for making the derivatives described herein are known in the art (see e.g., U.S. Pat. No. 7,309,795).

B. Drug Formulation

The compounds described above may be administered to patients in a pharmaceutical composition comprising the compound along with a pharmaceutically acceptable carrier. The carrier may be any solvent, diluent, liquid or solid vehicle that is pharmaceutically acceptable and typically used in formulating drugs. Guidance concerning the making of pharmaceutical formulations can be obtained from standard works in the art (see, e.g., *Remington's Pharmaceutical Sciences,* 16$^{th}$ edition, E. W. Martin, Easton, Pa. (1980)). In addition, pharmaceutical compositions may contain any of the excipients that are commonly used in the art. Examples of carriers or excipients that may be present include, but are not limited to, sugars (e.g., lactose, glucose and sucrose); starches, such as corn starch or potato starch; cellulose and its derivatives (e.g., sodium carboxymethyl cellulose, ethyl cellulose, or cellulose acetate); malt; gelatin; talc; cocoa butter; oils (e.g., peanut oil, cottonseed oil, safflower oil, sesame oil, olive oil, corn oil, or soybean oil); glycols; buffering agents; saline; Ringer's solution; alcohols; lubricants; coloring agents; dispersing agents; coating agents; flavoring agents; preservatives; or antioxidants. The compounds may also be made available as a dietary supplement in which they are combined with other additives or nutrients, preferably for oral administration.

It will be understood that pharmaceutical compositions or dietary supplements may contain any pharmaceutically acceptable, or isomeric, form of the compounds described herein, i.e., any form which maintains therapeutic activity and which does not cause unacceptable adverse effects when administered. For example, a compound may be in the form of a pharmaceutically acceptable salt or pro-drug.

Although dosage forms for oral delivery are generally preferred, the invention is compatible with the delivery of compounds by any route known in the art. Dosage forms that may be used include peroral, internal, rectal, nasal, lingual, transdermal, intravenous, intraarterial, intramuscular, intraperitoneal, intracutaneous and subcutaneous routes. Liquid dosage forms for oral administration include, but are not limited to, pharmaceutically acceptable emulsions, microemulsions, solutions, suspensions, syrups and elixirs. In addition to the active compounds, liquid dosage form may contain inert diluents commonly used in the art, such as, for example, water, or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, alcohols, polyethylene glycols, and fatty acid esters.

Injectable preparations may be in the form of sterile, injectable aqueous or oleaginous suspensions, diluents or solvents that may be used may include 1,3-butanediol, water, Ringer's solution and isotonic saline solutions. In addition, oils or fatty acids may be present. Although oral are generally preferred, patients with liposarcoma or lipomas or other fatty based tumors will preferably receive Rald, Rald-derived molecules or Raldh1 inhibitors directly by injection into the tumor.

Preferred oral dosage forms will be those are solid dosage forms such as capsules, tablets, pills, powders or granules. In these dosage forms, the active compound will typically be mixed with at least one inert, pharmaceutically acceptable excipient or carrier such as sodium citrate, or dicalcium phosphate and/or: fillers or extenders such as starches, lactose, sucrose, glucose, mannitol and silicic acid; binders such as, for example, carboxymethyl cellulose, alginates, gelatin, polyvinylpyrrolidinone, and acacia, humectants such as glycerol; disintegrating agents such as calcium carbonate, silicates or sodium carbonate; solution retarding agents such as paraffin; absorption accelerators such as quaternary ammonium compound; wetting agents such as cetyl alcohol or glycerol monostearate; absorbents such as kaolin; and lubricants, such as talc, magnesium stearate; sodium lauryl sulphate, etc. In addition, dosage forms may include buffering and flavoring agents.

C. Dosage

Pharmaceutical compositions (or dietary supplements) will typically be given to a patient in one or more unit dosage forms. A "unit dosage form" refers to a single drug administration entity, e.g., a single tablet, capsule or injection vial. The amount of compound present should be therapeutically effective, i.e., the amount should be sufficient to reduce insulin resistance, promote weight loss or prevent weight gain. This amount can vary widely and may be as low as 1-10 mg or as high as several grams.

D. Treatment Methods

General guidelines on the dosage of compounds to be given to a patient are provided above. However, exact dosages will depend upon the particular compound being given and will be determined using procedures well known in the art, balancing toxicity and therapeutic efficacy. Compounds may also be given to test animals to study their effect on weight gain and insulin resistance. In these cases, dosages are limited only by toxicity. It should also be recognized that inhibitory compounds may be administered as the sole active agents in a dosage form, or they may be combined with other drugs to improve overall effectiveness. Treatment should be continued until therapeutic objectives have been achieved. This may mean giving a compound for a few weeks to achieve a degree of weight gain or it may mean giving a compound indefinitely to prevent weight gain or prevent the development of insulin resistance.

E. Uses

As set forth above, the compounds described herein may be used for treating or preventing a disease or condition associated with adipogenesis or insulin resistance. However, experimental results indicating that retinaldehyde acts independently of retinoic acid by binding to PPARγ receptors and antagonizing their normal effects suggest that the compounds may also be useful in the treatment of diseases and conditions where activation of these receptors is a problem.

Examples

The present Example presents evidence that Rald is present in rodent fat, inhibits adipogenesis and suppresses peroxisome proliferator-activated receptor-γ and RXR responses. In vivo, mice lacking the Rald-catabolizing enzyme Raldh1 resist diet-induced obesity and insulin resistance and manifest increased energy dissipation. In ob/ob mice, administrating Rald or a Raldh inhibitor reduced fat and increased insulin sensitivity. These results identify Rald as a distinct transcriptionally-active regulator of metabolic responses to high fat diet.

A. Methods

Reagents

We obtained reagents and media from Sigma-Aldrich (St Louis, Mo.) and BioWhittaker (Walkersville, Md.) unless otherwise indicated. All media contained fungizone/penicillin/streptomycin. GlaxoSmithKline (PA, USA) provided BRL49653 (rosiglitazone). Unless otherwise indicated, retinoids used were all-trans isomers.

Animal Studies

Raldh1$^{-/-}$ mice (Molotkov, et al., *J. Biol. Chem.* 278:36085-90 (2003)) were compared to age-(8 weeks old) and sex-matched wild-type mice (5 males, 5 females/genotype). High-fat diet consisted of 45% fat/kcal, standard vitamin A 4 IU/g (D12451, Research Diet Inc., Canada). Water was ad libitum.

For fat distribution, B6.V-Lepob/J mice (5 groups of 3 females, 2.5 weeks old) received daily intraperitoneal injection (200 μL PBS, 3 weeks) containing vehicle (ethanol, 2 μL), retinoids (all-trans Rald, vitamin A, or all-trans RA, all 500 nM), or citral (10 μM) before sacrifice, storage (−20° C.) and MRI examination. The Standing Committee On Animals at Harvard Medical School approved all protocols.

Cell Culture

We cultured and differentiated mouse 3T3-L1 preadipocytes and primary fibroblasts isolated from 16-days old embryos using standard procedures (Green, et al., Cell 3:127-33 (1974)). After reaching confluence (DMEM, high glucose, 10% calf serum, Day 0), cells were differentiated (3-isobutyl-1-methylxanthine 0.5 mM, dexamethasone 1 μM, insulin 1.7

μM) for 48 h before media replacement every 48 h (DMEM, 10% FCS insulin, 1.7 μM) for 7 days.

Transient Transfections

Transient transfection of NIH 3T3 cells ($2.3 \times 10^4$ cells, 24-well plates) with PCMX-β-galactosidase and LBD/yeast Gal 4/luciferase constructs used Fugene (Roche) as before (Ziouzenkova, et al., *Proc. Natl. Acad. Sci. USA* 100:2730-5 (2003)). For siRNA transfections, 3T3-L1 cells (90% confluence, antibiotic-free DMEM, 10% CS, 24-well plates) received control (sequences C, D) or specific siRXRα and siRXRβ sequences (Santa Cruz) using Lipofectamine 2000/OptiMEM medium (Invitrogen) and media supplemented with 10% FBS 5 h post-transfection. Western blotting evaluated RXR levels post-transfection (48 h). After transfection (48 h), we induced differentiation before analysis after 7 days.

Human Recombinant RBP and Fluorescence Binding Assays

Human RBP4 and mouse CRBP1 subcloned in Pet and pET expression vectors respectively were expressed in *E. coli* then purified via Ni-NTA agarose resin (Invitrogen) with 6M urea as before but absent retinol (Xie, et al., *Protein Expr. Purif.* 14:31-7 (1998)). We dialyzed refolded protein against binding assay buffer (0.05M sodium phosphate, 0.15 M NaCl, pH 7.0) overnight, quantifying proteins at 280 nm (RBP440400 $M^{-1}$ $cm^{-1}$, CRBP1 26720 $M^{-1}$ $cm^{-1}$). We measured fluorescence on a luminescence spectrometer (Aminco, Spectronic Unicam, Rochester, N.Y.) equipped with magnetic stirring. Tryptophan fluorescence, monitored by excitation (285 nM) and emission (335 nM, both 0.05M sodium phosphate buffer, 0.15 M NaCl, pH 7.0), indicated retinol or Rald binding to RBP4 or CRBPI (1 μM).

Scintillation Proximity Assay (SPA)

Scintillation proximity assays were performed on our behalf. Human full-length PPARγ$_2$ was exposed to $^3H_2$-labeled known synthetic PPARγ agonists nTZD3 (Kd 2.5 nM) as before (Berger, et al., *Mol. Endocrinol.* 17:662-76 (2003)) in either the absence or presence of Rald.

RNA Analysis

We detected mouse Adh1, Raldh1, and β-actin RNA levels (total cell mRNA, RNeasy, Qiagen) using RT-PCR with the following specific primers:

```
Adh1:
5' ATG AGC ACT GCG GGA AAA GT     (SEQ ID NO: 1)

3' ACT TTA TTG GCC GTG TCT CTA A  (SEQ ID NO: 2)

Raldh1:
5' TGG GTT AAC TGC TAT ATC ATG TTG (SEQ ID NO: 3)

3' GGG TGC CTT TAT TAA GCT TTG CG  (SEQ ID NO: 4)
```

Northern blotting was performed as before with HyBond (Amersham; Ziouzenkova, et al., *Proc. Natl. Acad. Sci. USA* 100:2730-5 (2003)).

Protein and Intracellular Lipid Analysis

We determined triglyceride content in lysed cells (RIPA buffer, complete protease inhibitor cocktail, Roche) using an enzymatic colorimetric assay (Wako, Japan) and adiponectin levels via ELISA (R&D, Minneapolis). For Western blotting, cell lysates, plasma, and tissue lysates underwent reducing gel separation (10% acrylamide) and hybridization with RXR (Santa Cruz, Calif.), mouse RBP4 (Alpco), or UCP1 (Chemicon) antibodies.

LC-MS-MS Analysis

We reduced Rald to its stable oxime derivative with hydroxylamine (Molotkov, et al., *J. Biol. Chem.* 278:36085-90 (2003); von Lintig, et al., *Arch. Biochem. Biophys.* 385: 47-52 (2001)). Subcutaneous or visceral fat in mice (~200 μg, 129S3/SvImJ mice, 6 month males, n=4) and a New Zealand White male rabbit was dissected and immediately reduced. Atmospheric pressure chemical ionization in positive mode (Brucker Daltonics, Esquire LC) detected Rald oxime $(M+H)^+$ ion at m/z 300.

Magnetic Resonance Imaging (MRI)

MRI data (1 mm slices) obtained on a Bruker Avance 500 wide bore spectrometer (11.7 T; 500 MHz for proton) fitted with a gradient amplifier and a 30 mm "birdcage" transmitter/receiver coil was processed with Paravision™ software. Spin Echo parameters included TI weighted images: TE=15 ms and TR=300 ms, matrix=256, FOV=30 mm; RARE images: TE=51 ms, TR=2500 ms, matrix=256, FOV=30 mm. Abdominal fat measurements used axial slices (n=8) at the level of the left renal pelvis.

Dual-Energy X-Ray Absorptiometry (DEXA)

DEXA scans (high-fat diet, 180 days) used the GE Lunar Corporation PIXImus2 Dexa Scanner normalized by quality control plot (Charles River Laboratories).

Metabolic Parameters

After acclimation to powdered high fat diet (4 d), food/water intake, oxygen consumption, and carbon dioxide production were measured in metabolic cages (Ancare, Charles River Laboratories). Calculated metabolic rate (Weir equation) was expressed per g body weight. We performed insulin (ITT) and glucose tolerance tests (GTT) after food deprivation (16 h) using intraperitoneal insulin injection (ITT, 0.1 U/ml 0.005 ml/g body weight) or single 25% dextrose (GTT, 0.004 mL/g body weight) administration and glucometer measurements (Accu-Chek Advantage, Roche).

B. Results

Rald is Present in Rodent Fat

Rald is generated by the action of alcohol dehydrogenase-1 (Adh1) on retinol while Rald levels are determined in large part through Rald catabolism mediated by retinaldehyde dehydrogenase-1 (Raldh1). Both Adh1 and Raldh1 were differentially expressed during 3T3-L1 preadipocyte differentiation. While pre-adipocytes express mainly Adh1, differentiated 3T3-L1 cells express predominantly Raldh1, suggesting specific and temporally-regulated Rald production and catabolism in fat. These enzymes were also expressed in white fat from both lean (C56/BL6) and obese (age, sex-matched ob/ob mice). Adh1 expression was significantly higher in lean than in ob/ob mice, while differences in Raldh1 expression were not statistically significant between groups. The differential regulation of Adh1 and Raldh1 in lean versus genetically-obese mice also suggests Rald may have a functional role in fat tissue.

Rald is an unstable molecule, making its demonstration in tissues challenging. To counter this, Rald reduction to Rald oximes has been used to generate a stable biochemical Rald signature for purposes of quantification (Molotkov, et al., *J. Biol. Chem.* 278:36085-90 (2003); von Lintig, et al., *Arch Biochem Biophys* 385:47-52 (2001). We used this approach to measure the presence of Rald in fat from C57/BL6 mice on either a standard (lean) or high-fat diet for 180 days. Mice on high-fat feeding increased their weight two-fold as compared to those on regular chow. Equal amounts of fat tissue were dissected from mice, immediately reduced with hydroxylamine, and analyzed for levels of retinol (ROL) and Rald oxime using chromatographic and spectral analysis, with comparison to ROL and Rald oxime standards. This data revealed the presence of Rald in fat from lean and obese animals. Retinol levels were approximately 2.5 fold lower in obese versus lean animals while Rald content in fat from obese mice was even lower, decreased 5.4-fold as compared to lean mice. Rald was also present in rabbit fat, obviating any species-specific artifact. Mass spectrometric analysis confirmed the presence of similar signature Rald oxime structures in both a Rald oxime standard and pooled HPLC-purified Rald oxime fractions from wild-type rodent fat extracts. The identity of Rald oxime in fat is supported by the similar molecular weight of a protonated molecule at m/z 300, the loss of the oxime group at m/z 242, and the overall fragmentation pattern (94-208 m/z). Rald concentration in white fat ranged from 100 nM to ~1 µM based on analysis of 13 mice on regular chow.

The cognate interaction between retinoids and retinol binding proteins can influence levels and effects of retinoids both within and outside the cell. Using standard fluorescence quenching assays, Rald binding to human cellular retinol binding protein-1 (CRBP1) and retinol binding protein 4 (RBP4) was compared to the association between these binding proteins and retinol, their known binding partner (Vogel, et al., *J. Biol. Chem.* 276:1353-60 (2001); Berni, et al., *Faseb J* 7:1179-84 (1993)). All-trans Rald displayed a similar binding profile as all-trans retinol to both CRBP1 and RBP4. This data suggests mechanisms through which Rald may be bound and transported either intracellularly (CRBP1) or in the circulation (RBP4). Taken together, the expression of Rald generating/catabolizing enzymes in cultured and tissue adipocytes, the presence of free Rald in fat in vivo, and the existence of specific mechanisms for Rald transport all support a potential role for Rald in adipogenesis. The demonstration of Rald concentrations in fat also establishes the relevant concentrations at which to consider this possibility.

Rald Inhibits Adipogenesis In Vitro in a Manner Distinct from RA

To test Rald effects on adipogenesis, we performed 3T3-L1 mouse pre-adipocyte differentiation assays in the presence of Rald concentrations similar to those found in fat in vivo. Rald levels as low as 100 nM suppressed mRNA expression of the adipogenic target genes CD36, adiponectin, and aP2. These repressive effects of Rald were evident in a concentration-dependent manner in either the presence or absence of the PPARγ agonist BRL49653 (BRL), a potent adipogenic stimulus.

Since RA effects on adipogenesis vary as a function of differentiation stage (Xue, et al., *Mol. Cell. Biol.* 16:1567-75 (1996)), we compared the effects of 9-cis RA, all-trans RA (the most abundant RA form), and all-trans Rald in either early or late phase in adipocyte differentiation. Expression and release of the adipokine adiponectin is a sensitive indicator of adipogenesis. While 9-cis RA, all-trans RA, and all-trans Rald all inhibited adiponectin expression when added early (Day 0) to differentiating 3T3-L1 preadipocytes, the RA isomers had no effect when added later during differentiation (Day 2), responses consistent with the reported temporal expression of nuclear receptors like PPARγ and RXR during adipogenesis. In contrast to RA, nanomolar Rald concentrations also inhibited adipogenesis when added during later stages of differentiation. In these same experiments, Rald stimulation either early or late in adipocyte differentiation also decreased adiponectin secretion, doing so in a concentration-dependent manner. Indeed, nanomolar concentrations of Rald mitigated the six-fold increase in adiponectin levels induced by BRL stimulation. Consistent with these effects, Rald decreased lipid accumulation in 3T3-L1 pre-adipocyte differentiation in both the absence and presence of BRL.

Rald and RA Induce Distinct Nuclear Receptor Responses

Given Rald's suppression of PPARγ agonist-stimulated adipogenesis and adiponectin release, we tested if Rald altered activation of RAR and RXR, and if it did so in a way distinct from other retinoids. Ligand binding domain (LBD)-GAL4 transfection assays were performed in 3T3-NIH fibroblasts in the presence or absence of known specific nuclear receptor agonists and/or Rald. As previously reported (Repa, et al., *Proc. Nat'l Acad. Sci. USA* 90:7293-7 (1993)), all-trans Rald weakly activated the RARα-LBD but did not alter RARα-LBD activation by its known ligand 9-cis RA. Rald alone had no effect on RXRα-LBD activation. In contrast to RARα-LBD responses, Rald significantly inhibited RXRα-LBD activation by 9-cis RA. Thus, Rald plays a distinct, independent role from RA in RXRα-LBD regulation, suppressing ligand-mediated activation.

Given these effects of Rald on RXR-LBD activation, we next tested if Rald could inhibit activation of a transfected canonical PPAR response element (PPRE) luciferase construct after RXR and/or PPARγ transfection and respective agonist stimulation (9-cis RA or BRL). Rald significantly inhibited PPRE activation by both agonists, with the most potent effects seen after PPARγ and RXR co-transfection and PPARγ agonist stimulation (60% inhibition). Given these results, we used cell-free radioligand displacement assays (Berger, et al., *Mol. Endocrinol.* 17:662-76 (2003)) to consider direct interaction between PPARγ and all three major Rald isomers, namely 9-cis, 13-cis, and all-trans Rald. All three Rald isomers displaced high affinity PPARγ agonists (Kd=5.9±0.7, 9.7±1.2, and 11.9±1.9 µM for 9-cis, 13-cis, and all-trans Rald, respectively), consistent with direct but weak binding of these molecules to the PPARγ-LBD. Similar effects were evident in cell-based PPARγ-LBD assays in the presence of BRL. Thus, Rald suppresses adipogenic gene expression, adipocyte lipid accumulation, RXRα and PPARγ-LBD activation, as well as PPRE responses, all at concentrations (<1 µM) that overlap levels present in rodent fat in vivo. Importantly, these Rald effects diverge from the responses seen to RA. This data suggests that Rald is a biologically active mediator present in fat that may regulate adipogenesis through its action on RARα, RXRα, and PPARγ responses and in a manner independent of RA formation.

To evaluate Rald effects in an RXR loss of function model, 3T3-L1 adipogenesis assays in the presence of Rald were repeated but after first decreasing RXRα and RXRβ levels using siRNA to each RXR isotype. RXR is expressed early in adipogenesis (48 hours), helping initiate subsequent adipocyte differentiation, as evident in vitro (Canan, et al., *J. Med. Chem.* 42:742-50 (1999)) and in vivo (Imai, et al., *Proc. Nat'l Acad. Sci. USA* 98:224-8 (2001)). To explore the role of early RXR expression in mediating Rald effects on adipogenesis, 3T3-L1 pre-adipocytes were exposed to RXRα and RXRβ siRNA treatment (48 hours) prior to standard adipocyte differentiation (7 days). Triglyceride accumulation and adiponectin secretion were then measured as specific, distinct indicators of adipogenesis (Iwaki, et al., *Diabetes* 52:1655-63 (2003); Green, et al., *Cell* 3:127-33 (1974). After siRNA exposure, total RXR, including RXRα and RXRβ, was undetectable by Western blotting. As expected, RXRα/RXRβ siRNA-treated 3T3-L1 adipocytes manifest decreased triglyceride accumulation. Rald further decreased triglyceride accumulation even after siRNA exposure, suggesting RXR-independent effects of Rald on lipid accumulation in adipogenesis. In contrast, while RXRα/RXRβ siRNA significantly decreased adiponectin levels (~12 fold), Rald had no additional effects on adiponectin secretion, consistent with an RXR-dependent Rald effect. Collectively, this data suggests that Rald represses adipogenesis by both RXR-independent (triglyceride accumulation) and -dependent (adiponectin release) mechanisms.

Vitamin A Metabolism Regulates Adipocyte Biology In Vitro and In Vivo

Endogenous levels of Rald are dictated by enzymes controlling its production (Adh1) and catabolism (Raldh1). Raldh1-deficient (Raldh1$^{-/-}$) mice have been well-characterized as a model for Rald overproduction (Molotkov, et al., *J. Biol. Chem.* 278:36085-90 (2003)). These mice have impaired Rald oxidation, as evident in their markedly decreased RA and increased Rald levels while on a vitamin A-containing diet; Raldh1 deficiency has not been previously associated with a metabolic phenotype. Raldh1$^{-/-}$ mice fed a standard chow diet, which contains 4 IU vitamin A/g, had two-fold increased Rald plasma levels over matched wild-type controls (8.6±2.6 and 3.8±2.6 nM, respectively). To evaluate if Raldh1 deficiency also affected fat cell differentiation, adipogenesis assays were performed in primary fibroblasts isolated from Raldh1$^{-/-}$ and wild-type embryos (Day 16). Adipogenesis was markedly decreased in Raldh$^{-/-}$ as compared to wild-type cells, as evident on oil red 0 staining for lipid accumulation. The quantitative change in adipogenesis was evident in the two-fold decrease in adiponectin secretion in Raldh1$^{-/-}$ versus wild-type cells, a difference that was even more pronounced after treatment with BRL at all concentrations tested (~3-fold less at 300 nM BRL in Raldh1$^{-/-}$ versus wild-type cells). Higher BRL concentrations (10 µM) were able to overcome these Rald effects on adiponectin suppression and lipid accumulation, suggesting Rald responses are mediated at least in part through PPARγ responses. Mass spectroscopy analyses demonstrated the presence of Rald in white fat from wild-type mice (242.9 m/z, n=12). Fat from Raldh1$^{-/-}$ mice contained more Rald (n=12). This spectral pattern was identical to that seen with a Rald oxime standard. This data in vitro and ex vivo suggests that higher Rald levels in fat tissue may affect adipocyte biology in Raldh1$^{-/-}$ mice in vivo.

To study the effects of Rald on adipogenesis in vivo, wild-type and Raldh1$^{-/-}$ mice were placed on a high-fat diet (45% fat, standard vitamin A 41 U/g). Weight was measured weekly until sacrifice (6 months) and subsequent tissue analysis. White fat of Raldh1$^{-/-}$ mice had significantly higher levels of retinol (52%) and Rald (two-fold) as compared to wild-type mice. Adipocytes from Raldh1$^{-/-}$ fat were also two-fold smaller in size as compared to wild-type. In these same fat samples, adipocyte size correlated inversely with Rald levels. This data supports Rald as a regulator of adipocyte formation in vivo.

Raldh1 Regulates Lipid and Glucose Metabolism

The differences seen in adipose tissue between Raldh1$^{-/-}$ and wild-type mice on high fat diet would be predicted to have systemic metabolic consequences. Indeed, after high fat feeding (6 months), Raldh1$^{-/-}$ animals gained significantly less weight (93%) than wild-type mice (mean weight gain wild-type 26.6±1.9 g versus Raldh1$^{-/-}$ 13.7±3.6 g); two randomly selected females from each genotype are shown. Interestingly, Raldh1$^{-/-}$ females had a significantly greater decrease in weight than males (relative to the corresponding wild-type gender mice, 2.3-versus 1.7-fold, P<0.001). Since metabolic parameters related to fat can vary between sexes, more detailed analyses of metabolism were performed in wild-type and Raldh1$^{-/-}$ females (n=5/genotype). DEXA scanning revealed that the differences in weight between wild-type and Raldh1$^{-/-}$ mice resulted from decreased whole body fat accumulation. One otherwise healthy Raldh1$^{-/-}$ female was sacrificed at the end of the study but prior to tissue and plasma analysis due to a greater than 20% weight loss (as per IACUC guidelines). The greater decrease in white fat accumulation in Raldh1$^{-/-}$ versus wild-type mice was evident in dissected fat pads from both subcutaneous and visceral depots (4.2- and 3.9-fold decrease respectively). Raldh1$^{-/-}$ mice also had significantly lower plasma free fatty acid levels than wild-type mice (0.21±0.1 versus 0.53±0.3, respectively, P<0.04, Wilcoxon rank test). Livers from Raldh1$^{-/-}$ mice also had decreased lipid accumulation versus wild-type mice, as evident on H&E staining and total liver weight.

The differences in fat accumulation in Raldh1$^{-/-}$ versus wild-type mice occurred despite similar food and water intake in both groups. These results suggest a shift in total energy balance in Raldh1 deficiency. Raldh1$^{-/-}$ mice demonstrated a higher metabolic rate, respiratory quotient, and a significantly increased body temperature compared to wild-type controls, identifying increased catabolism and thermogenesis as contributors to the decreased weight evident in these mice. Consistent with the role of thermogenesis in determining body weight, uncoupling protein 1 (UCP-1) levels in brown fat were significantly higher in Raldh1$^{-/-}$ than wild-type mice. Thus, increased Rald levels in Raldh1$^{-/-}$ mice were associated with both tissue-specific responses in fat (decreased adipocyte size) as well as with systemic changes in energy balance (thermogenesis).

Fat tissue is involved in the systemic regulation of glucose metabolism and insulin sensitivity. Many pathways contribute to this relationship including adipokines like adiponectin and leptin that help regulate insulin sensitivity. Recent work also identifies a role for RBP4 in increasing insulin resistance. Given our data for Rald repression of adiponectin expression and association with RBP4, these targets are potentially relevant to the metabolic changes seen in Raldh1$^{-/-}$ mice. Total adiponectin levels were significantly decreased (20%) in the plasma of Raldh1$^{-/-}$ mice, consistent with Rald's effects in vitro. Raldh1$^{-/-}$ mice also had markedly reduced leptin levels. RBP4 levels were significantly decreased in both male and female Raldh1$^{-/-}$ mice.

To evaluate the impact of Raldh1 deficiency and increased Rald levels on glucose metabolism, glucose and insulin tolerance tests were performed on these same high-fat fed Raldh1$^{-/-}$ and wild-type mice. Although as expected, high fat diet increased insulin resistance in wild-type mice, Raldh1$^{-/-}$ mice were protected from this response, with significantly lower glucose levels on both glucose and insulin tolerance tests. Insulin levels were not significantly different between animal groups. Taken together, these results suggest that Raldh1$^{-/-}$ mice are less susceptible to two key metabolic disturbances induced by high fat diet, namely obesity and insulin resistance.

To consider further the effects of Rald on fat accumulation as well as test if these metabolic changes derived from Rald itself and not subsequent RA generation or other vitamin A metabolites, we used ob/ob mice, a mouse model of obesity characterized by progressive weight gain on regular chow, to compare responses to administration of Rald, the Rald parent compound vitamin A, all-trans RA, or citral, a known inhibitor of Raldh enzymes (weekly intraperitoneal injections; both retinoids 500 nM, citral 10 µM, equal to 240 nmol/g). After 3 weeks, subcutaneous fat mass was quantified by magnetic resonance imaging (MRI). The extent of visceral fat accumulation in these mice precluded accurate quantitative measurement. Mice receiving Rald had significantly less subcutaneous fat as apparent from the largest residual fat pad in these animals. There was a lower percentage of subcutaneous fat relative to total body fat in mice receiving either Rald (15.5±0.6%) or citral (14.8±0.6%) as compared to vehicle (18.8±1.4%), vitamin A (17.3±1.3%), and atRA groups (19.1±1.6%, all less than P<0.05). Rald administration also repressed adipogenesis in preadipocytes isolated from human visceral fat depots. Given this response and the changes in visceral and subcutaneous fat seen in Raldh1$^{-/-}$ mice, Rald effects are not likely restricted to subcutaneous fat.

RBP4 levels also varied in ob/ob mice exposed to these different retinoids, with unique responses to Rald modulation. While RA as compared to vehicle had no effect on RBP4 levels, vitamin A increased RBP4 plasma levels two-fold. In contrast, both Rald and citral significantly suppressed circulating RBP4 levels (as compared to vehicle), recapitulating the RBP4 pattern seen in Raldh1$^{-/-}$ mice. Consistent with the changes seen in adiposity and RBP4, both Rald and citral administration improved glucose tolerance in ob/ob mice. The differences seen in the genetic absence of Raldh1 and after administration of Rald versus vitamin A or atRA argue against these effects deriving simply from Rald metabolism into RA or vitamin A. Together these findings identify a distinct role of Rald in adipose tissue with concomitant systemic effects on obesity and insulin sensitivity.

C. Discussion

The present Example demonstrates that Rald, rather than serving as a precursor for RA, plays a distinct and unique role in adipocyte differentiation in vitro and in systemic lipid accumulation and insulin resistance seen in response to a high fat diet in vivo. Intracellular Rald is present in fat at submicromolar levels (~1 nmol/g) and can interact with CRBP1 and RBP4, binding proteins involved in respective intracellular and circulating retinoid transport. When Rald concentrations are increased, either in the absence of Raldh1 or after direct Rald administration, fat formation is decreased. Inhibition of Rald catabolism (citral treatment) had similar effects. These findings identify a novel role for Rald in adipocyte biology and adipose tissue. Changes in Rald concentrations were also associated with systemic changes in insulin sensitivity and metabolic homeostasis in mice. Despite the widely held assumption that Rald outside of the eye serves mainly as a precursor for RA, the divergence in effects seen here with Rald versus RA in vitro and in vivo argues for Rald itself as a previously unrecognized biologically active mediator in fat.

Rald's unique effects on adipokines, adipogenesis, and body weight focus attention on those parameters regulating the relative cellular concentrations of Rald and RA. The balance between Rald and RA is likely determined by factors including the vitamin A concentration, the expression and activity of enzymes that metabolize Rald and RA, other retinol-modifying enzymes like esterases/hydrolases, retinol binding proteins (RBPs/CRBPs), as well as the redox status in cells. Each of these factors may have functional consequences, as seen with the recent reported association between RBP4 and diabetes in both animals and humans (Yang, et al. *Nature* 436:356-62 (2005); Graham, et al., *N. Engl. J. Med.* 354:2552-63 (2006)). In terms of enzymes metabolizing Rald, we uncovered an unrecognized metabolic phenotype seen in the genetic absence of Raldh1, with marked alterations in fat accumulation, glucose homeostasis, and adipokine production in Raldh1$^{-/-}$ mice after high-fat feeding. These metabolic changes are likely due, at least in part, to the increased levels of Rald in fat demonstrated here, especially since direct administration of Rald reproduces the metabolic profile evident in Raldh1$^{-/-}$ mice. Importantly, direct administration of RA and Rald have divergent effects in vitro and in vivo, further supporting a role for Rald that is distinct from its function as an RA precursor.

The metabolic changes induced by either Rald administration or in the genetic absence of Rald catabolism have multiple potential clinical implications. Our findings identify Rald generation as a novel factor that may influence responses to vitamin A, RA, or other retinoid-based therapy. The presence of Rald in fat and its association with RBP4 suggest Rald as a potential contributor to the relationship between RBP4 and insulin sensitivity. At concentrations similar to those found in vivo, Rald opposes BRL-stimulated adipocyte responses, suggesting that endogenous Rald levels could influence clinical responses to PPARγ agonists.

Rald appears to exert its effects through both RXR-dependent and independent mechanisms. Rald represses adiponectin production but not after RXR expression has been reduced. In contrast, Rald-mediated repression of triglyceride accumulation persists regardless of RXR expression. Rald can inhibit LBD activation and cellular responses to both RXR and PPARγ agonists. Although Rald binds weakly to the RXR- and PPARγ-LBDs, it potently suppresses adipogenesis in vitro and in vivo. Interestingly, selective synthetic PPAR and RXR modulators reportedly have similar divergence between potency of receptor binding and adipogenic effects (Yamauchi, et al., *J. Clin. Invest.* 108:1001-13 (2001)). Various mechanisms may underlie how certain molecules influence nuclear receptor responses independent of receptor binding potency, including conformational changes in the receptor, salt bridge formation, accessory molecule recruitment/release, or post-translation protein modification.

These studies provide a novel link between vitamin A metabolism and responses to high fat diet as well as its complications of obesity and insulin resistance. In the absence of an inducible enzyme of vitamin A metabolism Raldh1, mice are protected from dietary-mediated obesity and insulin resistance. This impact of Raldh1 on metabolism and obesity suggests Raldh1 as a potential candidate for therapeutic targeting and/or a source of variation in body weight. In the models studied here, Rald concentrations in vivo correlate tightly with changes in fat accumulation and metabolic responses, providing one likely explanation for the metabolic phenotype of Raldh1-deficient mice. Rald is present in adipose tissue of rodents at concentrations that have potent and unique functional effects on adipogenesis in vitro and in vivo.

In the absence of Raldh1, energy balance appears shifted towards increased energy dissipation, as suggested by the increased body temperature, metabolic rate and UCP1 expression manifest in these animals. Interestingly, in some animal models, increased UCP1 has not been associated with increased respiratory quotient. Regardless, the changes in energy balance seen with Rald could result from its actions in various Rald- and RA-sensitive tissues including brown fat, immune cells, and the central nervous system (CNS).

The linear relationship between Rald concentrations and adipocyte size, the lower concentrations of Rald in obese as compared to lean mice, the impaired adipogenesis seen in Raldh1$^{-/-}$ preadipocytes all suggest Rald's effects in adipose tissue likely contribute to the protection against diet-induced obesity and insulin resistance evident in Raldh1-deficient mice. Certainly Rald's actions in adipose tissue can also provide feedback to other systems, including the CNS and the immune system, with subsequent effects on adipose biology. Taken together, these findings support Rald as a biologically active metabolic mediator with unique effects separate from its serving as a source for RA formation.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

What is claimed is:

1. A method of treating a patient for type 2 diabetes, comprising administering to said patient a therapeutically effective amount of a pharmaceutical composition, wherein said pharmaceutical composition is in unit dosage form and comprises:
   a) one or more active agents wherein said active agents inhibit retinaldehyde dehydrogenase1 (Raldh1), and are solely compounds of formula II:

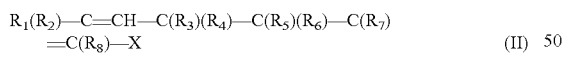

$R_1(R_2)-C=CH-C(R_3)(R_4)-C(R_5)(R_6)-C(R_7)=C(R_8)-X$     (II)

wherein $R_1-R_8$ is selected from: H, Cl; F; $NO_2$; I; Br; a straight or branched $C_1$-$C_6$ alkyl optionally substituted at one or more carbons with a substituent selected from: Cl; F; $NO_2$; I; Br; a $C_1$-$C_3$ alkyl; a straight or branched $C_2$-$C_6$ alkenyl optionally substituted at one or more carbons with a substituent selected from: Cl; F; $NO_2$; I; Br; a $C_1$-$C_3$ alkyl;
   X is C(=O)H; CN; or C(=O)R wherein R is a $C_1$-$C_3$ alkyl; and
   b) a pharmaceutically acceptable carrier;
   wherein the one or more active agents of a) are the sole active agents.

2. The method of claim 1, wherein at least one of $R_1$, $R_2$, and $R_7$ is $CH_3$.

3. The method of claim 1, wherein at least two of $R_1$, $R_2$, and $R_7$ are $CH_3$.

4. The method of claim 1, wherein $R_1$, $R_2$, and $R_7$ are all $CH_3$.

5. The method of claim 4, wherein at least one of $R_3$-$R_6$ and $R_8$ is H.

6. The method of claim 4, wherein at least two of $R_3$-$R_6$ and $R_8$ are H.

7. The method of claim 4, wherein at least three of $R_3$-$R_6$ and $R_8$ are H.

8. The method of claim 4, wherein at least four of $R_3$-$R_6$ and $R_8$ are H.

9. The method of claim 4, wherein $R_3$-$R_6$ and $R_8$ are all H.

10. The method of claim 9, wherein X is C(=O)H.

11. The method of claim 1, wherein $R_3$-$R_6$ and $R_8$ are all H.

12. The method of claim 11, wherein at least one of $R_1$, $R_2$, and $R_7$ is $CH_3$.

13. The method of claim 1, wherein at least two of $R_1$, $R_2$, and $R_7$ are $CH_3$.

14. The method of claim 13, wherein X is C(=O)H.

15. The method of claim 1, wherein X is C(=O)H.

16. The method of claim 15, wherein $R_3$-$R_6$ and $R_8$ are all H.

17. The method of claim 16, wherein at least one of $R_1$, $R_2$, and $R_7$ is $CH_3$.

18. The method of claim 1, wherein said pharmaceutical composition is administered to said patient orally.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
atgagcactg cgggaaaagt                                                   20

<210> SEQ ID NO 2
<211> LENGTH: 22
<212> TYPE: DNA
<213> ORGANISM: Homo sapiens

<400> SEQUENCE: 2
actttattgg ccgtgtctct aa                                                22

<210> SEQ ID NO 3
<211> LENGTH: 24
<212> TYPE: DNA
<213> ORGANISM: Homo sapiens

<400> SEQUENCE: 3
tgggttaact gctatatcat gttg                                              24

<210> SEQ ID NO 4
<211> LENGTH: 23
<212> TYPE: DNA
<213> ORGANISM: Homo sapiens

<400> SEQUENCE: 4
gggtgccttt attaagcttt gcg                                               23
```